(12) United States Patent
Dupire et al.

(10) Patent No.: US 11,819,844 B2
(45) Date of Patent: Nov. 21, 2023

(54) IN VITRO SYSTEM FOR EVALUATING THE EFFECTIVENESS OF A DEODORANT

(71) Applicant: MICROFACTORY, Paris (FR)

(72) Inventors: Jules Dupire, Paris (FR); Fabrice Monti, Saulx les Chartreux (FR); Patrick Tabeling, Paris (FR)

(73) Assignee: MICROFACTORY, Paris (FR)

( * ) Notice: Subject to any disclaimer, the term of this patent is extended or adjusted under 35 U.S.C. 154(b) by 1368 days.

(21) Appl. No.: 16/096,465

(22) PCT Filed: Mar. 24, 2017

(86) PCT No.: PCT/EP2017/057050
§ 371 (c)(1),
(2) Date: Oct. 25, 2018

(87) PCT Pub. No.: WO2017/186423
PCT Pub. Date: Nov. 2, 2017

(65) Prior Publication Data
US 2019/0118176 A1    Apr. 25, 2019

(30) Foreign Application Priority Data
Apr. 27, 2016  (FR) ..................................... 1653752

(51) Int. Cl.
*B01L 3/00*    (2006.01)
*G01N 33/487*  (2006.01)
*G01N 33/15*   (2006.01)

(52) U.S. Cl.
CPC ....... *B01L 3/502715* (2013.01); *B01L 3/5027* (2013.01); *G01N 33/15* (2013.01);
(Continued)

(58) Field of Classification Search
CPC ....... B01L 3/502715; B01L 2200/0605; B01L 2300/023; B01L 2300/0861; B01L 2300/14; B01L 2400/082
See application file for complete search history.

(56) References Cited

U.S. PATENT DOCUMENTS

| 4,884,438 A | 12/1989 | Jones et al. | |
| 6,632,619 B1 * | 10/2003 | Harrison | B01L 3/5027 436/805 |
| 2016/0082433 A1 * | 3/2016 | Baltenneck | G01N 33/4875 422/503 |

FOREIGN PATENT DOCUMENTS

WO    2014/170174 A1    10/2014

OTHER PUBLICATIONS

Zeng et al., 2015 International Conference on Fluid Powder and Mechatronics, 2015, pp. 711-715. (Year: 2015).*

(Continued)

*Primary Examiner* — Allison M Fox
*Assistant Examiner* — Qing Xu
(74) *Attorney, Agent, or Firm* — Sughrue Mion, PLLC (57) ABSTRACT

A process for evaluating efficacy of a deodorant product includes: introducing sweat into a main channel formed in a fluidic device satisfying particular requirements; measuring a flow rate of the sweat in the main channel and transmitting the flow rate to a controller; imposing a pressure set point on the pressure actuator by closed-loop control so the flow rate of the sweat in the main channel is controllable; contacting the sweat and a deodorant product and reacting the sweat and the deodorant product with each other, the deodorant product being provided in a particular manner, wherein while the sweat and the deodorant product react with each other, the flow rate of the sweat in the main channel is maintained at substantially zero; and determining at least (Continued)

one of a physicochemical parameter and a biological parameter of a product of the reaction between the sweat and a the deodorant product.

15 Claims, 5 Drawing Sheets

(52) U.S. Cl.
CPC .... *G01N 33/48707* (2013.01); *B01L 2200/0605* (2013.01); *B01L 2300/023* (2013.01); *B01L 2300/0627* (2013.01); *B01L 2300/0861* (2013.01); *B01L 2300/14* (2013.01); *B01L 2400/082* (2013.01)

(56) References Cited

OTHER PUBLICATIONS

Callewaert et al., Arch Dermatol Res, 2014, 306:701-710. (Year: 2014).*
Burry et al., International Journal of Cosmetic Science, 2001, 23(4): 207-210. (Year: 2001).*
Hou, et al., "Artificial microfluidic skin for in vitro perspiration simulation and testing", Lab on a Chip: Miniaturisation for Chemistry, Physics Biology, Materials Science and Bioengineering, Mar. 18, 2013, pp. 1868-1875, vol. 13, No. 10, XP055328483 (9 pages total).
Communication dated Dec. 14, 2016, from the National Institute of Industrial Property in counterpart French application No. 1653752.
International Search Report, issued by International Searching Authority in corresponding International Application No. PCT/EP2017/057050, dated Apr. 21, 2017.

* cited by examiner

IN VITRO SYSTEM FOR EVALUATING THE EFFECTIVENESS OF A DEODORANT

CROSS REFERENCE TO RELATED APPLICATIONS

This is a National Stage of International Application No. PCT/EP2017/057050 filed Mar. 24, 2017, claiming priority based on French Patent Application No. 1653752 filed Apr. 27, 2016.

FIELD OF THE INVENTION

The present invention applies to the fields of cosmetics, pharmacy and medicine. It concerns a system for evaluating the efficacy of a deodorant and more precisely a system allowing in vitro modelling of the interaction between sweat and a deodorant.

BACKGROUND

Deodorants limit body odours by preventing the bacterial decomposition of perspiration. Antiperspirants, a subgroup of deodorants, regulate and/or stop the release of sweat on the skin. This reduction or cessation of perspiration may be achieved by choosing a deodorant containing aluminium salts, such as aluminium hydrochloride, and/or zirconium salts. To block the emission of sweat, a deodorant can cause a plug to form in a sweat pore. One of the mechanisms proposed to explain the formation of this plug involves a step of formation of flocs in a sweat pore, i.e. an agglomeration of sweat proteins into particles capable of clogging a pore. Other mechanisms have been proposed to explain the formation of these plugs.

The French Health Products Safety Agency (AFSAPS) reports toxicity in some patients from repeated exposure to aluminium and recommends the use of antiperspirants with a mass concentration of aluminium salt of less than 2%, whereas it is generally between 5% and 20% in products on the market, depending on the application methods concerned (Risk assessment related to the use of aluminium in cosmetic products, AFSAPS, 2011).

This health risk leads to a general technical objective including producing an effective antiperspirant-type deodorant having lower concentrations of aluminium hydrochloride than commercial deodorants, even though deodorants are less effective at low concentrations of aluminium hydrochloride. This problem can be solved in different ways. For example, other deodorant products can be used. For example, WO 2010017609 discloses antiperspirant products containing an agonist of TRMP8 ion channels to reduce the production of sweat. It is also possible to screen those molecules most likely to be antiperspirants among a wide range of molecules. For example, WO 2015072970 discloses measuring the potential to evaluate the efficacy of an antiperspirant product, this potential being correlated with the flocculation kinetics of sweat proteins in contact with an antiperspirant product.

WO 201417010174 discloses a microfluidic system, wherein channels capable of transporting sweat are connected to a channel suitable for the flow of a product containing an antiperspirant product. The interaction of sweat and liquid antiperspirant causes the formation of a plug that can be observed by imaging. On the one hand, this method does not make it possible to evaluate the most common dosage forms of antiperspirant products. On the other hand, the sweat pores are modelled by microfluidic channels whose width may be of the order of ten micrometres. In practice, it is problematic to successfully move a meniscus (fluid-air interface), formed by the injection of sweat into a channel, to the exact junction point with a channel capable of transporting a liquid perspirant, and to stabilize it at this point. Indeed, a small variation in the volume of injected sweat, for example of the order of ten picolitres, can cause a displacement of the meniscus by about a hundred micrometres.

To bring the meniscus to a junction point and stabilize it, a first solution is injecting sweat into a channel, the injection being carried out by a flow source, for example a syringe pump, and then cutting off the fluidic connection between the flow source and the channel, for example by means of a stopcock. In this case, it is not possible to control the sweat injected into the channel once the connection is cut, particularly if the fluidic connection and the channel are made of rigid material. The meniscus may move freely, and it is not possible to control the location of the reaction with an antiperspirant product.

A second solution is injecting sweat into a channel with a flow source, for example a syringe pump, then imposing a zero flow rate by controlling the flow source. Syringe pumps may for example be characterized by the actuation of very low flow rates, for example of the order of 1 pL/s. However, the stabilization time of a syringe pump is too long (for example of the order of a few minutes) to be able to stabilize the position of the meniscus at the junction between two channels.

A third solution is injecting sweat into a channel using a pressure actuator (or pressure controller). A pressure actuator can impose a pressure, for example greater than atmospheric pressure, to the gas phase of a gastight reservoir in which a source of liquid sweat is arranged. This imposed pressure allows sweat to be injected into a channel connected to the sweat of the reservoir. Pressure actuators are characterized by a shorter response time than flow sources. However, a pressure actuator allows the application of flow pressures in only one direction. It is not possible to impose both positive and negative pressures with the same actuator without compromising with a longer response time.

In addition, mechanical (for example elastic) relaxation of the material forming the fluidic channels and/or fluidic connectors (for example due to a variation of pressure or temperature) may cause flow drift despite the imposition of a zero flow rate by a flow source or a pressure actuator. Finally, capillary phenomena can create microscopic pressure variations in the vicinity of the meniscus, causing movement of the meniscus and preventing its stabilization. In fact, the experimental conditions of the plug formation study are difficult to reproduce, sensitive and difficult to stabilize.

The instability of a meniscus at a junction point also prevents in vitro evaluations of a deodorant of a type other than an antiperspirant. It presents a technical problem for the study of antibacterial products or hybrid products containing antibacterials and antiperspirants.

BRIEF SUMMARY

The present disclosure relates to a method and a system which aims to remedy some or all of the above-mentioned disadvantages, and more particularly to create a system capable of maintaining a sweat meniscus at the end of a channel capable of transporting sweat, with a zero and stable flow rate with no time limit compared with the time of an experiment to evaluate the efficacy of one or more deodorant products.

An in vitro system for evaluating the efficacy of a deodorant product comprises:
- at least one fluidic device comprising at least one main channel having an inlet at one end and capable of circulating natural or artificial sweat;
- at least one reservoir capable of containing natural or artificial sweat and a gas phase, separated by an interface at a height h1,
- at least one connecting channel connected to the reservoir and to the inlet of at least one said main channel;
- a pressure actuator capable of imposing the pressure of a gas phase inside said reservoir;
- at least one flow meter;
- at least one closed-loop controller;
- the flow meter being capable of measuring the flow rate of the main channel and transmitting information about said flow rate to the controller, the controller being capable of transmitting control information to the pressure actuator, the main channel having an orifice formed by its wall at its other end, at a height $h_2$, the height $h_1$ being strictly different from 112.

Advantageously, $h_2$ is strictly greater than $h_1$ and the pressure actuator of the system is capable of imposing a pressure greater than atmospheric pressure in the reservoir.

Advantageously, the fluidic device of the system comprises a plurality of main channels, the main channels being independent.

Advantageously, the maximum width of the orifice of the system is less than or equal to 1 mm.

Advantageously, the fluidic device of the system is arranged in an enclosure in which at least one element selected from humidity and temperature is controlled.

Advantageously, a fluidic device of the system comprises a first monolithic part comprising the main channel and at least one substantially flat outer face, each orifice coinciding with the outer face.

Advantageously, the fluidic device comprises at least one sensor selected from a pH sensor, an amino acid sensor, a nucleotide sensor, an enzyme sensor and a bacteria sensor, each the sensor being arranged on a surface selected from a wall of the main channel and the outer face.

A process for evaluating the efficacy of a deodorant product implemented by a system comprising at least one fluidic device comprising at least one main channel, each main channel having an inlet at one end and having an orifice formed by the wall of said main channel at another end at a height $h_2$, said system comprising at least one reservoir capable of containing natural or artificial sweat and a gas phase, separated by an interface at a height $h_1$, $h_1$ being strictly different from $h_2$, said process comprising at least the steps of:
- introducing natural or artificial sweat into the whole of the main channel by imposing a pressure in the gas phase of a reservoir containing said sweat, with a pressure actuator, said reservoir being fluidically connected to said main channel;
- measuring a sweat flow rate of the main channel, transmitting information about the flow rate to a controller, the controller imposing a pressure set point on the pressure actuator, so as to impose a substantially zero flow rate on the main channel by closed-loop control;
- bringing the sweat and a deodorant product into contact on either side of at least one said orifice;
- waiting during the course of a reaction between the sweat and the deodorant product;
- determining at least one parameter selected from a physicochemical parameter and a biological parameter characteristic of the reaction between the sweat and the deodorant product.

Advantageously, the deodorant product is in a dosage form selected from at least a gel, a cream, an emulsion, a foam and an anhydrous solution.

Advantageously, the process comprises a step of absorbing the sweat in contact with the orifice outside the main channel, between the second step and the third step of a process according to the claim.

Advantageously, the fourth step of the process of at least increasing the pressure of the gas phase, measuring the flow rate of the main channel and measuring the pressure of the gas phase during a substantial variation of the flow rate of the main channel.

Advantageously, the formation of the plug is observed by imaging during the fourth step of the process.

Advantageously, the second step of the process is carried out by spraying the deodorant product onto the orifice.

Advantageously, the process implements the fluidic device comprising a first monolithic part, the first part comprising the main channel and at least one substantially flat outer face, the orifice coinciding with the outer face and the step of bringing the sweat and a deodorant product into contact on either side of at least one orifice is carried out by depositing the deodorant product on the substantially flat outer face.

Advantageously, the fifth step of the process comprises measuring the pH of at least one element selected from the sweat, the deodorant product and a product of the reaction between the sweat and the deodorant product.

Advantageously, the fluidic device is substantially transparent and the fifth step of the process comprises measuring an element selected from the transmission and reflection of a light illumination emitted towards at least one element selected from the sweat, the deodorant product and a product of the reaction between the sweat and the deodorant product.

Advantageously, the fifth step of the process comprises detecting the presence of bacteria in at least one element selected from the sweat, the deodorant product and a product of the reaction between the sweat and the deodorant product.

Advantageously, the third step of the process is carried out by depositing a shim of thickness $t_1$ on the outer face, the shim being perforated above at least one the orifice, and scraping a deodorant product on the shim so as to deposit a layer of deodorant product substantially of thickness $t_1$ above at least one the orifice.

BRIEF DESCRIPTION OF THE DRAWINGS

The present disclosure will be better understood, and other advantages, details and features of the disclosure will become apparent, during the following explanatory description, made by way of example with reference to the appended drawings wherein.

DETAILED DESCRIPTION

Natural sweat 5 is defined as a biological fluid secreted by the sweat glands during sweating. Natural sweat 5 was for example collected beforehand from a human being by any method known to the skilled person.

Artificial sweat 5 is defined as sweat 5 comprising for example elements such as sodium chloride (NaCl), lactic acid, urea, bovine serum albumin (BSA), ammonia in an amount sufficient to achieve a substantially neutral pH and water. Alternatively, any other type of artificial sweat known to the skilled person may be used in the context of the invention.

Figure 1:
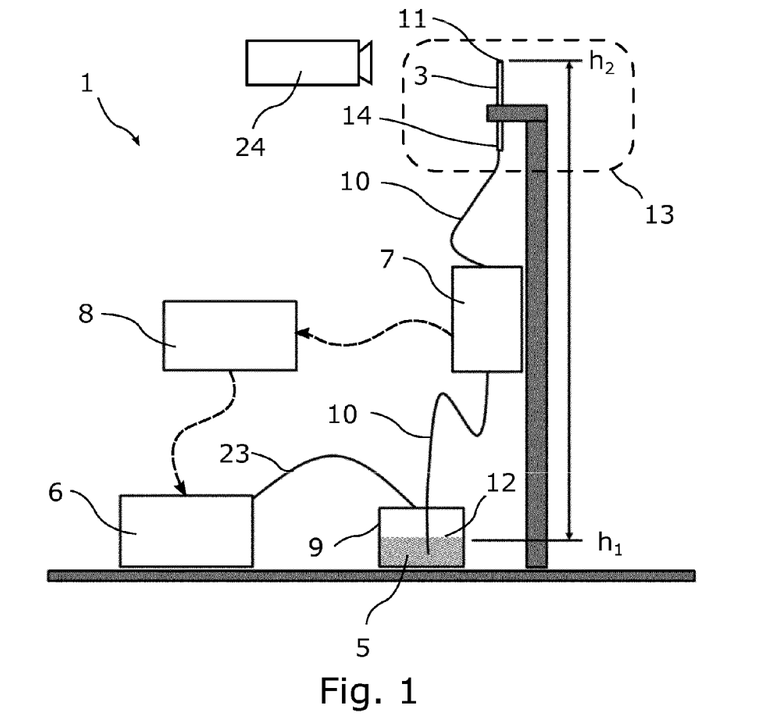
FIG. 1 is a schematic representation of an in vitro system 1 for evaluating the efficacy of a deodorant product 2.

FIG. 1 is a schematic representation of an in vitro system 1 for evaluating the efficacy of a deodorant product 2, according to one embodiment of the invention.

The system 1 comprises a pressure actuator 6, also called a pressure controller, capable of applying pressure to one or more outputs. The pressure actuator 6 may have a plurality of outputs in which the pressures imposed are independent and/or coupled. An outlet of the pressure actuator 6 is connected to pressure-imposition tubing 23, itself connected to a reservoir 9. In this way, the pressure actuator 6 imposes the pressure of a gas phase of a reservoir 9.

System 1 also comprises at least one reservoir 9 capable of containing natural or artificial sweat 5 and a gas phase. The liquid phase, i.e. the sweat 5, and the gas phase, typically air, are separated by an interface 12 at a height $h_1$. Typically, a reservoir may contain between 0.1 mL and 100 mL of sweat 5.

Pressure-imposition tubing 23 is connected to the gas phase of a reservoir 9 through an opening in the reservoir 9. Thus, the pressure actuator 6 can impose a pressure in the gas phase of a reservoir 9. If the pressure imposed is greater than atmospheric pressure, the corresponding overpressure may be between 0 bar and 20 bar and preferentially between 0 bar and 2 bar. Typically, a pressure variation may be imposed in the gas phase by the pressure actuator 6 in less than 200 ms, preferentially in less than 100 ms and preferentially in less than 50 ms.

A connecting channel 10 is connected to a reservoir 9 through an opening in the reservoir 9 to allow one end of the connecting channel 10 to be arranged in the sweat 5. The reservoir remains sealed against any gas phase of the external environment in this arrangement. Alternatively, a connecting channel 10 may be connected to an opening in a reservoir 9 in contact with the sweat 5. The connecting channel 10 connects the reservoir 9 to the inlet 14 of a main channel 4.

A connecting channel 10 is defined as a channel, a tube or a hose, which is for example flexible, allowing the reservoir 9 to be connected to the inlet 14. A connecting channel 10 is also defined as any succession of channels connected in series allowing the reservoir 9 to be connected to the inlet 14, for example a hose connected to a metal sleeve, or a hose connected to the channel of a measuring instrument itself connected to another hose.

The system 1 also comprises a fluidic device 3. A fluidic device 3 comprises at least one main channel 4, capable of circulating sweat 5. The main channel 4 comprises an inlet 14 at one end and has an orifice 11, formed by its wall at its other end. This orifice 11 may be viewed as a model of the end of a sweat duct in contact with the external environment. In all embodiments of the invention, an orifice 11 is arranged at a height $h_2$, strictly different from the height $h_1$ defined above. For example, the difference $\Delta h$ between $h_2$ and $h_1$ may be between 1 cm and 3 m, preferentially between 5 cm and 1 m and preferentially between 10 cm and 50 cm.

Thus, by imposing a pressure greater than atmospheric pressure in the gas phase of the reservoir 9, the sweat 5 from the reservoir 9 can be injected into a connecting channel then into a main channel 14 of the fluidic device 4, up to an orifice 11. At the height $h_2$ of an orifice 11, a fluid particle is subjected to at least two forces: a force due to the pressure imposed by the pressure actuator 6, entraining a fluid particle towards the outside of the main channel 14 in the case of an imposed pressure greater than atmospheric pressure, and a hydrostatic force, entraining a fluid particle towards the inside of the main channel in the case of a positive $\Delta h$ value. These two forces may be in opposite directions and allow a fine equilibration of the pressure to be imposed by the pressure actuator 6 in order to maintain the meniscus at the height of an orifice 11 by creating a closed control loop. Theoretically, the equilibration pressure $\Delta P_{stop}$ may be expressed as $\Delta P_{stop} = \rho \cdot g \cdot \Delta h$ where $\rho$ is the mass density of the sweat 5 and g is the absolute value of gravitational acceleration.

In order to achieve a closed control loop, the system 1 comprises at least one flow meter 7. A flow meter 7 is arranged in the system 1 so as to measure a flow rate or a flow rate equivalent to the flow rate of a main channel 14. For example, a flow meter 7 can be arranged so as to measure the flow rate of a connecting channel 10 or to be capable of measuring the flow rate in a connecting channel 10. The flow meter 7 can determine the flow directions by transmitting a positive or negative value of the measured flow rate and preferentially allows the flow rate to be measured in a range between −60 μL/min and 60 μL/min.

A system 1 also comprises a closed-loop controller. A controller 8 may for example be implemented by a computer or a suitable electronic circuit. A flow meter 7 is capable of transmitting information about, or a measurement of, the flow rate of a main channel 4 or of the connecting channel 10 to the controller 8. A controller 8 is capable of controlling, or transmitting control information to, the pressure actuator 6. The user may give an instruction, for example a flow rate instruction, to the controller 8. A zero flow rate instruction may for example be given to maintain a meniscus precisely at the height $h_2$ of an orifice 11. Closed-loop control of the flow rate of a main channel 4 is achieved by the action of the pressure force imposed on the sweat 5 and the feedback from the hydrostatic force imposed on the sweat 5. Advantageously, a controller 8 of the system 1 is a proportional-integral-derivative (PID) controller. A zero flow rate control loop for a main channel 4 may for example be implemented as follows: a flow meter 7 transmits information about the flow rate at time t to a controller 8. If the flow rate is positive, the controller 8 regulates the pressure actuator 6 so as to reduce the imposed pressure. If the measured flow rate is negative, the controller 8 regulates the pressure actuator 6 so as to increase the imposed pressure.

This operation may be repeated automatically a large number of times (for example more than ten times) so as to converge on a flow rate of zero or sufficiently close to zero. Sufficiently close to zero means that the absolute value of the average flow rate, measured for example as a running average over one second, is less than or equal to 0.200 µL/min, preferentially less than or equal to 0.1 µL/min and preferentially less than or equal to 0.05 µL/min.

In general, the system makes it possible to parallelize flow control of a plurality of main channels 4. A fluidic device 3 advantageously comprises a plurality of independent, i.e. non-interconnected, main channels 4, each of the channels having an inlet 14 and an orifice 11. The different outputs of a pressure actuator 6 may independently control the pressures imposed in a plurality of different reservoirs 9. Each reservoir 9 may be connected to a different inlet 14 via a different connecting channel 10. A plurality of flow meters may each independently measure the flow rate of a different connecting channel 10 and transmit flow rate information to a controller 8 with several inputs. The controller 8 may have several outputs connected to at least one pressure actuator 6. In this way, it is possible to multiplex the evaluation of the efficacy of a deodorant product 2 by using several orifices 11. It is for example possible to evaluate the effect of different types of sweats 5 with regard to the same deodorant product 2 and/or the effect of several deodorant products 2 with regard to a single type of sweat 5 and/or to vary the type of sweat 5 and the type of deodorant product 2 during the same experiment.

The system may also include an enclosure 13 with controlled humidity and/or temperature, in which a fluidic device 3 is arranged. Evaporation, controlled in part by the imposed temperature and humidity conditions, is, at this scale, a factor capable of significantly varying the position of the sweat 5 meniscus when injected and stabilized at the level of an orifice 11. The enclosure 13 with controlled humidity and/or temperature allows experimental conditions in which it is possible to limit or at least control this evaporation.

The system may also include a microscopic imaging device 24, capable of imaging one or more orifices 11 during or after the evaluations of the deodorant product 2. A fluidic device 3 may be transparent: in this case, the microscopic imaging device may also make it possible to observe a main channel 4 during an evaluation of a deodorant product 2.

Figure 2:
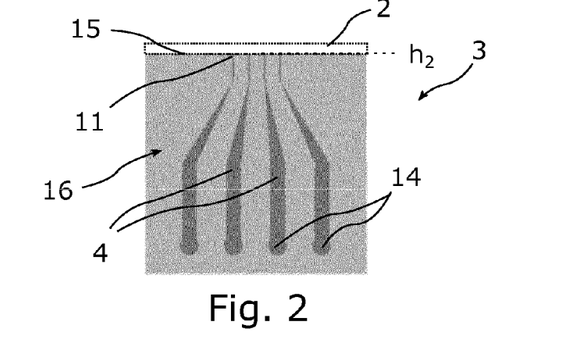
FIG. 2 is a schematic representation of a fluidic device 3.

FIG. 2 is a schematic representation of a section of a fluidic device 3. A fluidic device 13 according to one embodiment of the invention comprises at least one main channel 4 capable of circulation sweat 5. FIG. 2 shows a section of a fluidic device 3 comprising four main channels 4. The section is selected so as to show the geometry of each of the main channels 4. Each main channel 4 comprises an inlet 14 at one end and an orifice 11 formed by its walls at another end, at a height $h_2$. In one variant, the height of each of the orifices 11 may be substantially different from that of the other orifices 11, but always different from the height $h_1$.

In one embodiment of the invention, the fluidic device 3 may comprise a first monolithic part 16 comprising the main channel 4. The first part 16 may comprise a substantially flat outer face 15, each orifice 11 coinciding with the outer face 15. This outer face 15 may allow the application of a deodorant product 2 in dosage forms other than a liquid form. It may be viewed as an experimental skin model for evaluating a deodorant product 2. Substantially flat means that it be comprised locally in a main plane; it may be smooth, or structured and/or textured in such a way as to mimic the contours of the skin. Different dosage forms may be advantageously selected from a gel, a cream, an emulsion, a foam and an anhydrous solution. This feature solves the problem of the prior art of not being able to evaluate dosage forms of a deodorant product 2 other than the liquid form. FIG. 2 shows for example a layer of deodorant product 2 deposited on an outer face 15. This layer 2 covers at least one orifice 11, and particularly all the orifices 11 in the illustration in FIG. 2.

A sensor may be advantageously arranged on a surface of the first part 16, in particular on a wall of a main channel 4 and/or an outer face 15. A sensor may be used to determine a physicochemical or biological parameter before, after or during a reaction between a sweat 5 and a deodorant product 2. Advantageously, a sensor may be capable of measuring a pH, a presence or type of amino acids, a presence or type of nucleotides, an enzyme and/or a bacterium or a population of bacteria. Without limiting the type of sensor used, a sensor may be capacitive, electrochemical, resistive and may be implemented in a fluidic device 3 for example by microfabrication of a metal electrode. A sensor may be particularly useful for characterizing the antibacterial properties of a deodorant product 2 that is devoid of antiperspirant action and does not cause the formation of a plug 25 and/or of particles formed by flocculation.

Figure 3:
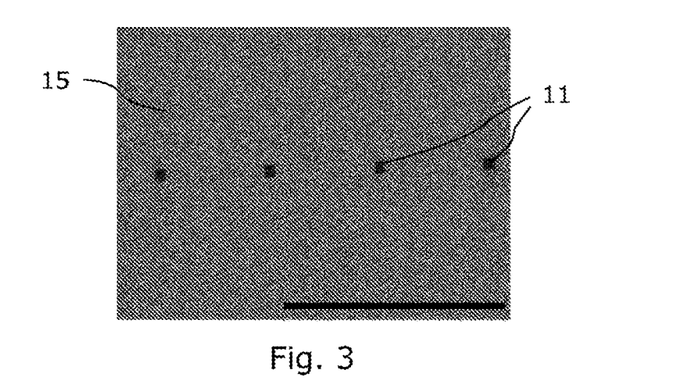
FIG. 3 is a photograph taken by a scanning electron microscope showing orifices 11 of a fluidic device 3.

FIG. 3 is a photograph taken by a scanning electron microscope showing orifices 11 of a fluidic device 3. More specifically, FIG. 3 shows four orifices 11, coinciding with a flat outer face 15. The scale bar in the photograph, at the bottom right, corresponds to a length of 1 mm. Advantageously, the maximum width of an orifice 11 is less than 1 mm. It is preferentially between 1 µm and 1 mm and preferentially between 5 µm and 200 µm. FIG. 3 shows square orifices 11, each side of which measures substantially 60 µm and the maximum width of which is substantially 85 µm. Orifices 11 may be arranged in a linear array, as shown in FIG. 3, or in a matrix. These configurations can make it possible to increase the density of clogging experiments carried out per unit area, for example by using the same deposit of deodorant product 2, and thus to obtain statistically more reliable information on the parameters to be measured during experiments to evaluate a deodorant product 2.

Figure 4:
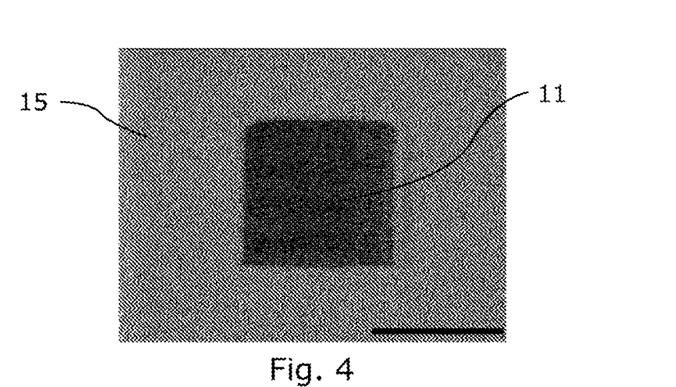
FIG. 4 is a photograph taken by a scanning electron microscope showing an orifice 11 of a fluidic device 3.

FIG. 4 is a photograph taken by a scanning electron microscope showing an orifice 11 of a fluidic device 3. This photograph is an enlargement of the photograph shown in FIG. 3. The scale bar in the photograph, at the bottom right, corresponds to a length of 50 µm. The first part 16 of the fluidic device 3 may be monolithic, i.e. made of a block and/or of continuous material. The first part 16 may be made of polymeric and preferably elastomeric material. FIG. 3 and FIG. 4 show a first part 16 made of polydimethylsiloxane (PDMS). The use of a polymer can make it possible to create orifices 11 coinciding with a locally flat outer face 15. Walls of a main channel 4 may for example be made from a mould by polymerization of a first layer of PDMS. A second, flat layer of PDMS may be joined to the first layer, for example by a partial curing method or by surface treatment of at least one of the surfaces of the two layers with an oxygen plasma to form the last wall of a main channel 4. Finally, the block thus obtained may be cut in a plane corresponding to a normal section of a main channel 4 at the level of an orifice 11, so as to form the orifices 11 and the flat outer face 15. The first part 16 may also be made of rigid polymer, for example cyclic olefin copolymer (COC). In one variant, the first part 16 may be made of metal.

Figure 5:
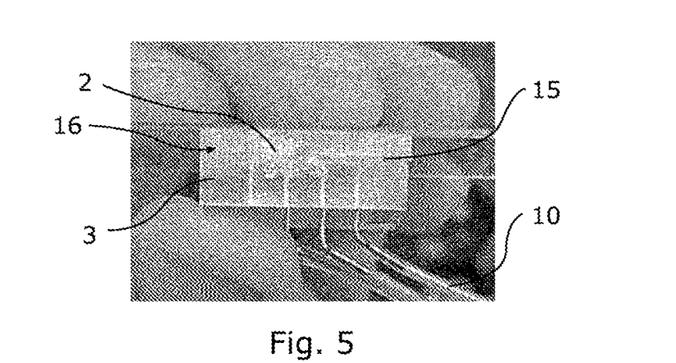
FIG. 5 is a photograph showing a fluidic device 3 and connecting channels 10.

FIG. 5 is a photograph showing a fluidic device 3 and connecting channels 10. In this photograph, a first part 16 includes four main channels 4 connected to four connecting channels 10 (one of which is not visible in FIG. 5). FIG. 5 shows a flat surface 15 covered with a layer of deodorant product 2 at least on one orifice (not visible at this scale).

Figure 6:
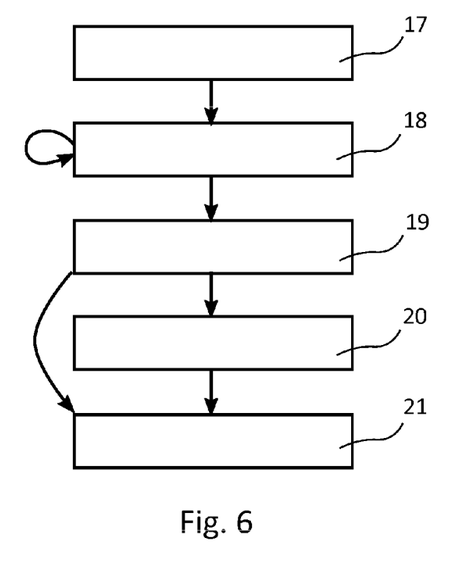
FIG. 6 is a diagram showing a process for measuring efficacy of a deodorant.

FIG. 6 is a diagram showing a process according to one embodiment of the invention. A process for evaluating a deodorant product 2 according to one embodiment of the invention will comprise at least the following steps:

a first step 17 includes introducing (or injecting) natural or artificial sweat 5 into the whole of a main channel 4, by imposing a pressure in the gas phase of a reservoir 9 comprising sweat 5, with a pressure actuator 6, the reservoir 9 being connected to the main channel 4. "The whole" means that sweat 5 is injected from the inlet of a main channel 4 to its orifice 11 or further. The sweat may for example overflow a main channel 4 from the orifice 11;

a second step 18 includes measuring a flow rate of sweat 5 of the main channel 4, transmitting information about the flow rate to a controller 8, the controller imposing a pressure set point on the pressure actuator 6 so as to impose a substantially zero flow rate on the main channel 4 by closed-loop control. This step may be considered as a step of stabilizing the flow at a zero flow rate. For example, if the flow rate is strictly positive, the closed control loop reduces the pressure imposed by the pressure actuator 6. This loop may be repeated a large number of times, preferably greater than 10, before measuring a flow rate sufficiently close to zero, i.e. whose absolute value of the average flow rate, measured for example as a running average over a second, is less than or equal to 0.200 µL/min, preferentially less than or equal to 0.1 µL/min and preferentially less than or equal to 0.05 µL/min. Once the flow has stabilized, the pressure imposed by the pressure actuator 6 may be kept constant and/or readjusted during the process by repeating this step;

a third step 19 includes bringing the sweat 5 and a deodorant product 2 into contact on either side of the orifice(s) 11. In general, a deodorant product 2 may be deposited on the orifices 11. The sweat 5 and the deodorant product 2 being brought into contact, a reaction may be initiated between the two.

a fourth step 20 includes waiting during the course of a reaction between the sweat 5 and the deodorant product 2. This step may, more particularly, include waiting during the formation of a plug 25 produced by a reaction between the sweat 5 and the deodorant product 2, which in this case is of the anti-perspirant type. The deodorant product 2 may not be effective enough to allow the formation of a plug 25: this step then consists only in waiting for a time determined by the user, sufficient to conclude as to the efficacy of a deodorant product 2;

a fifth step 21 includes determining a parameter selected from a physicochemical parameter and a biological parameter characteristic of a reaction between a sweat 5 and the deodorant product 2. In the case of an antiperspirant product, this step may include in determining at least one physicochemical parameter characteristic of the plug 25 and/or of the reaction between the sweat 5 and the deodorant product 2.

In the case of an antibacterial deodorant product 2, this step may include measuring the absence or presence of a bacterial population in a sweat 5, a deodorant product 2 and/or a reaction product, or in quantifying this bacterial population.

In general, the steps may be implemented consecutively. Alternatively, the fifth step 21 may be carried out in parallel with the fourth step 20. This variant may advantageously correspond to a step during which the formation of a plug 25 is observed by imaging, for example by means of a microscopic imaging device 24. Alternatively, the fifth step may be carried out in parallel with all the other steps of the process according to one embodiment.

The fifth step 21 of a process according to one embodiment may advantageously comprise measuring the pH of a sweat 5 and/or of a deodorant product 2 and/or of the product of a reaction between the two, before, during and/or after this reaction. This measurement may be used to check that the pH of the sweat 5, of a deodorant product 2 and/or of a product of a reaction between the two is within a pH range compatible with the skin. This measurement may be made by a sensor arranged in a fluidic device 3 as previously described, or by other means, such as measurement of a wavelength emitted by a colorimetric pH indicator introduced into a sweat 5 and/or a deodorant product 2.

The fifth step 21 of a process according to one embodiment may advantageously comprise measuring the transmission, reflection, diffusion and/or absorption, for example at a specific wavelength, of a sweat 5 and/or of a deodorant product 2 and/or of the product of a reaction between the two. This measurement may be made using a microscopic imaging device 24 and a substantially transparent fluidic device 3, for example made of PDMS. In the case of the presence of colloidal particles suspended in the sweat 5 and/or a deodorant product 2, this step may correspond to measuring the turbidity of one of the phases contained in a first part 16 or on the surface of a first part 16. This measurement can detect the presence of particles produced by a reaction between a sweat 5 and a deodorant product 2.

The fifth step 21 may also comprise measuring the presence, the type and/or the number of bacteria in a sweat 5, a deodorant product 2 and/or a product of a reaction between the two. In this way, information on the efficacy of an antibacterial deodorant product can be accessed by measuring the growth of a bacterial population in a fluidic device 3 mimicking the skin.

Advantageously, the sweat 5 in contact with an orifice 11 outside a main channel 4 may be absorbed, for example between the second step 18 and the third step 19. Absorption may be carried out by the user. It may be carried out for example for a controlled and repeated length of time between experiments. Given the small volume exiting a main channel 4 during the first injection step 17, it is also possible to wait for the sweat 5 outside a main channel 4 to evaporate.

Advantageously, the third step 19 may be carried out by depositing a deodorant product 2 on the substantially flat outer face 15. The deposition of a deodorant product 2 on the skin is mimicked in this way. In this step, the face 15 may be comprised in a horizontal plane: in this way, all of the orifices 11 may be at the same height. The face 15 may also be oriented differently, for example, comprised in a vertical plane.

Figure 7:
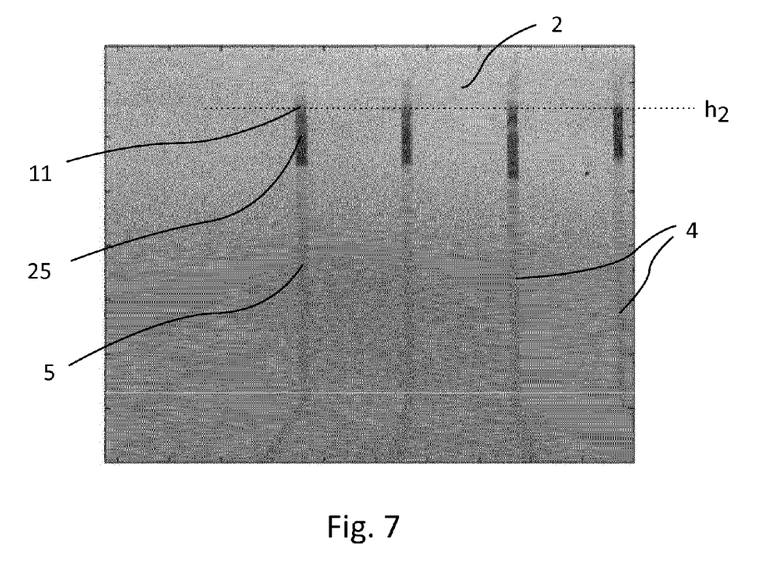
FIG. 7 is a photomicrograph showing the formation of plugs 25 in a fluidic device 3.

FIG. 7 is a photomicrograph showing the formation of plugs 25 in a fluidic device 3. In this embodiment, the fluidic device 3 is transparent, in this case made of PDMS. The black dotted line corresponds to the outer face 15 coinciding with the orifices 11, at a height $h_2$. The photograph in FIG. 7 is taken after bringing the sweat 5 into contact with a layer of deodorant product 2. The darker parts of the main channels 4 correspond to the plugs 25 formed by a reaction between the sweat 5 and a deodorant product 2. The lighter parts of the main channels 4 correspond to the liquid sweat 5. The kinetics of formation of plugs 25 may be measured by filming this part of the system 1 during the fourth step 20 of waiting.

Figure 8:
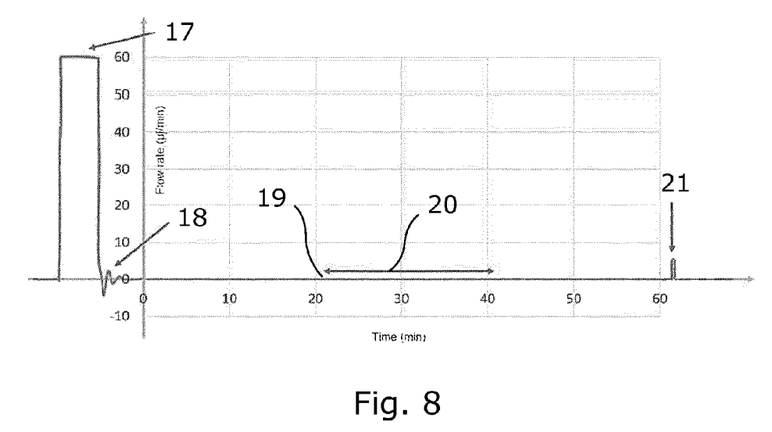
FIG. 8 is a diagram showing a measurement of the flow rate in a main channel 4 as a function of time during the implementation of a process for measuring efficacy of a deodorant.

FIG. 8 is a diagram showing a measurement of the flow rate in a main channel 4 as a function of time during the implementation of a process according to one embodiment. The peak flow rate forming an interval of negative time values corresponds to an injection or introduction of sweat 5 into a connecting channel 10 and into a main channel 4, i.e. to a first step 17 of the process. During the second step 18 of the process, the stabilization of the flow rate of a main channel 4 at a substantially zero value by closed-loop control corresponds to the oscillations in the flow rate measurement. A third step 19 of bringing a deodorant product 2 into contact with sweat 5, at a time substantially equal to 20 minutes, is not visible when measuring the flow rate, meaning that the stabilization of the flow rate is effective. The double-headed arrow corresponds to the waiting time of the fourth step 20, during which the deodorant product 2 is brought into contact with the sweat 5. In general, the waiting time in the fourth step of the process may be greater than 10 minutes, preferably greater than 20 minutes and preferentially greater than 1 hour. It may also be equal to several days, for example two days. The peak flow rate observable at a time greater than 60 minutes corresponds to a fifth step 21, in which includes measuring a physicochemical parameter characteristic of a formed plug, in this case the unclogging pressure of the main channel 4.

Figure 9:
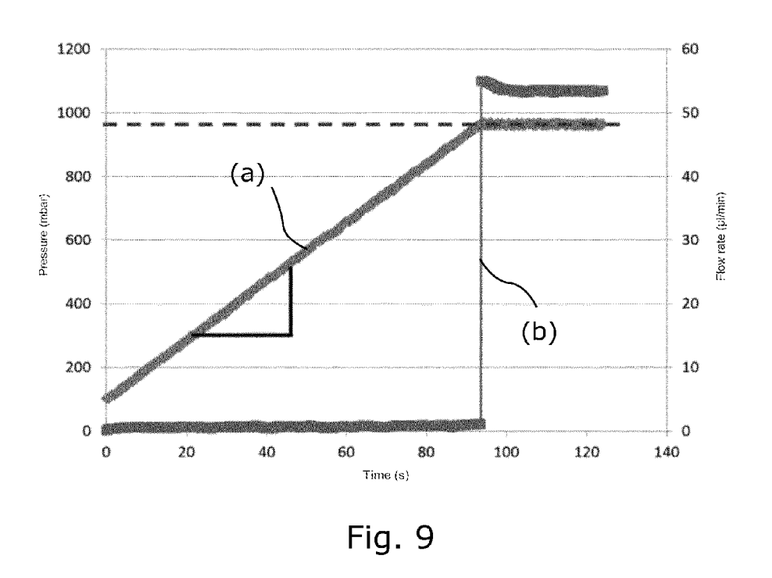
FIG. 9 is a diagram showing a measurement of the unclogging pressure.

FIG. 9 is a diagram showing a measurement of the unclogging pressure. This measurement may correspond to a fifth step 21 and may be carried out after a fourth step of waiting. The curve (a) in FIG. 9 shows a measurement of the pressure (of the gas phase of the reservoir 9) imposed by a pressure actuator 6 over time in a main channel 4 containing a plug 25. The ordinate of the curve (a) is shown to the left of the diagram. The curve (b) in FIG. 9 shows a measurement of the flow rate of the same main channel 4 over time. The ordinate of the curve (b) is shown to the right of the diagram. The pressure imposed by the pressure actuator 6 is increased in a first phase. In the implementation of the fifth step of the process, shown in FIG. 9, the pressure is increased linearly. It may also be increased quadratically, exponentially, logarithmically or by time interval. The flow rate is measured simultaneously in the same main channel 4. During the pressure increase phase, the flow rate remains substantially zero due to the resistance formed by the plug 25. The beginning of a second phase corresponds to the unclogging of the main channel 4, marked by a substantial variation, preferentially a dramatic increase in the measured flow rate. The unclogging of the main channel 4 corresponds to the moment when the flow rate of the main channel exceeds a threshold value. This threshold value may be equal to 45 µL/min. It depends on the geometry of a main channel 4, the sweat 5 and the deodorant product 2 used. The sampling of the flow rate measurement of the main channel may be carried out at a frequency of 10 Hz.

Figure 10:
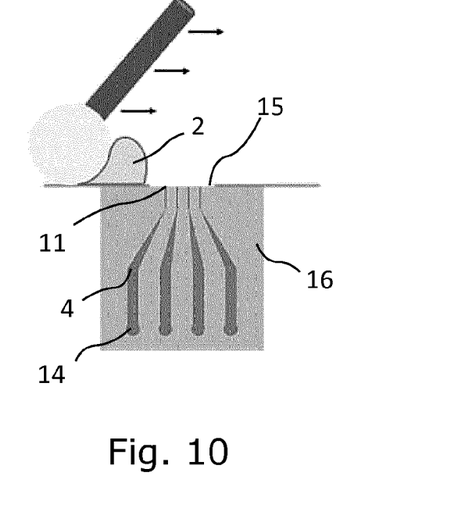
FIG. 10 shows a method of depositing and contacting a deodorant product 2 with sweat 5.

FIG. 10 shows a method of depositing and contacting a deodorant product 2 with sweat 5. The usual dosage forms of deodorant products 2 may be deposited on part of the outer face 15 coinciding with orifices 11. Dosage forms of type roll-on (deposited by means of a ball) and type soft solid emulsion (emulsion whose mechanical properties are modified by surfactants or waxes) may be deposited in a substantially uniform manner by scraping. A shim of thickness $t_1$ ($t_1$ being for example substantially equal to 50 µm) may be placed on the outer face 15 of a first part 16 of a fluidic device 3, the shim being perforated above the orifice(s) 11. A shim may for example be made of adhesive tape. A deodorant product 2 can be scraped over the shim, the scraping movement being symbolized in FIG. 10 by the black arrows. A substantially uniform layer of thickness $t_1$ can thus be applied to the orifice(s) 11. The uniformity of the deposition of antiperspirant product 2 on a plurality of orifices 11 makes it possible to carry out, in parallel, series of experiments under substantially identical conditions.

In other embodiments, a deodorant product 2 may be brought into contact with the sweat 5 by spraying the deodorant product 2 onto the orifices 11. This method makes it possible to mimic the spray dosage form available on the market. For example, a perforated shim may be placed over orifices 11. The sprayer may be placed at a distance suitable for depositing a deodorant product 2 with a substantially homogeneous density on the perforated part of a shim. Preferentially, the sprayer may be tilted, for example by 45°, during the spraying of the deodorant product 2.

In addition, the inventors note that the features of the system 1, of the device 3 and of the process according to embodiments of the disclosure may be applied to a system for evaluating the clogging of a syringe. Indeed, a plug may be formed at the orifice of a syringe containing a product in liquid form, for example by drying. A characterization of a drying and/or of a plug may be carried out by measuring the unclogging pressure as described in FIG. 9. Moreover, the imposition of a zero flow rate by a closed-loop control system can make it possible to carry out repeatable evaluations of the drying and the unclogging of a syringe. It would be sufficient to replace the fluidic device 3 with a syringe to obtain a system for evaluating the clogging of a syringe. Similarly, it would be sufficient to replace the fluidic device 3 with a syringe, the sweat 5 with a liquid to be injected and to not bring the liquid into contact with a deodorant product 2 to obtain a process for evaluating the clogging of a syringe.

The invention claimed is:

1. A process for evaluating efficacy of a deodorant product comprising:
    introducing natural or artificial sweat into a main channel formed in a fluidic device, the main channel extending from an orifice formed in a first part of the fluidic device to an inlet of the fluidic device, the orifice of the main channel being located at a height $h_2$ over a surface, the sweat being initially disposed in a reservoir, the reservoir also comprising a gas phase, an interface between the sweat and the gas phase in the reservoir is located at a height $h_1$ over the surface, the height $h_1$ being different from the height $h_2$, the sweat introduced into the main channel by imposing a pressure in the gas phase of the reservoir with a pressure actuator, the reservoir being fluidically connected to the main channel;
    measuring a flow rate of the sweat in the main channel and transmitting the flow rate to a controller;
    imposing, by using the controller, a pressure set point on the pressure actuator by closed-loop control such that the flow rate of the sweat in the main channel is controllable;
    spraying a deodorant product onto the first part in which the orifice is formed, so as to deposit the deodorant product on a side of the first part opposite which the main channel extends within the fluidic device;
    contacting the sweat and the deodorant product and reacting the sweat and the deodorant product with each other, wherein, while the sweat and the deodorant product react with each other, the flow rate of the sweat in the main channel is maintained at zero; and determining at least one parameter selected from a physicochemical parameter and a biological parameter of a product of the reaction between the sweat and the deodorant product.

2. The process according to claim 1, wherein contacting the sweat and the deodorant product and reacting the sweat and the deodorant product with each other comprises forming a plug in the main channel.

3. The process according to claim 1, further comprising absorbing the sweat in contact with the first part of the fluid device outside of the main channel.

4. The process according to claim 1, wherein imposing, by using the controller, the pressure set point on the pressure actuator comprises increasing the pressure on the gas phase in the reservoir.

5. The process according to claim 2, further comprising observing formation of the plug with an imaging device.

6. The process according to claim 1, wherein the first part comprises a flat outer face that coincides with the orifice, and further comprising depositing the deodorant product on the flat outer face that coincides with the orifice, so as to carry out the contacting the deodorant product and the sweat and the reacting the deodorant product and the sweat with each other.

7. The process according to claim 1, further comprising measuring the pH of at least one of the sweat, the deodorant product and the product of the reaction between the sweat and the deodorant product.

8. The process according to claim 1, wherein the fluidic device is transparent, and wherein determining the at least one parameter comprises measuring transmission and reflection of light illumination emitted toward the fluidic device to observe the sweat, the deodorant product and the product of the reaction between the sweat and the deodorant product.

9. The process according to claim 1, further comprising detecting the presence of bacteria in at least one of the sweat, the deodorant product and the product of the reaction between the sweat and the deodorant product.

10. The process according to claim 6, wherein depositing the deodorant product comprises depositing the deodorant product on the flat outer surface using a shim having a thickness $t_1$, the shim being perforated above at the orifice, and further comprising scraping the deodorant product on the shim so as to deposit a layer of the deodorant product having a thickness equal to the thickness $t_1$ on the flat outer surface.

11. The process according to claim 1, further comprising increasing the flow rate of the sweat in the main channel such that the product of the reaction between the sweat and the deodorant product is removed from the main channel.

12. The process according to claim 1, wherein determining the at least one parameter comprises determining the at least one parameter while reacting the deodorant product and the sweat.

13. A process for evaluating efficacy of a deodorant product, comprising:

introducing natural or artificial sweat into a main channel formed in a monolithic part of a fluidic device, the main channel extending from an orifice that is formed in a flat outer face of the monolithic part to an inlet of the fluidic device, the orifice located at a height $h_2$ over a surface, the sweat being initially disposed in a reservoir, the reservoir also comprising a gas phase, an interface between the sweat and the gas phase in the reservoir is located at a height $h_1$ over the surface, the height $h_1$ being different from the height $h_2$, the sweat introduced into the main channel by imposing a pressure in the gas phase of the reservoir with a pressure actuator, the reservoir being fluidically connected to the main channel;

measuring a flow rate of the sweat in the main channel and transmitting the flow rate to a controller;

imposing, by using the controller, a pressure set point on the pressure actuator by closed-loop control such that the flow rate of the sweat in the main channel is controllable;

contacting the sweat and a deodorant product and reacting the sweat and the deodorant product with each other, wherein the deodorant product is deposited on the flat outer face that coincides with the orifice, such that the deodorant product contacts and reacts with the sweat; and determining at least one parameter selected from a physicochemical parameter and a biological parameter of a product of the reaction between the sweat and the deodorant product.

14. The process according to claim 13, wherein the flow rate of the sweat in the main channel is maintained at zero while the sweat and the deodorant product react with each other.

15. The process according to claim 13, wherein contacting the sweat and the deodorant product and reacting the sweat and the deodorant product with each other comprises forming a plug in the main channel.

\* \* \* \* \*